United States Patent [19]
Wang et al.

[11] Patent Number: 5,630,423
[45] Date of Patent: May 20, 1997

[54] METHOD OF MEASURING TISSUE OPTICAL PROPERTIES USING AN OPTICAL BEAM OF OBLIQUE INCIDENCE AND USES THEREOF

[76] Inventors: Lihong Wang, 1404 E. Circle #B, College Station, Tex. 77840; Steven L. Jacques, 4302 Compton Cir., Bellaire, Tex. 77401

[21] Appl. No.: 594,757

[22] Filed: Jan. 31, 1996

[51] Int. Cl.⁶ ........................................... A61B 5/00
[52] U.S. Cl. ........................................... 128/664; 128/665
[58] Field of Search .................................. 128/664, 665; 356/338, 340, 446

[56] References Cited

U.S. PATENT DOCUMENTS 5,452,723  9/1995  Wu et al. ................................ 128/664

*Primary Examiner*—Marvin M. Lateef
*Assistant Examiner*—Eleni Mantis Mercader
*Attorney, Agent, or Firm*—Benjamin Aaron Adler

[57] ABSTRACT

The present invention provides a method of determining the reduced scattering coefficient of a turbid medium having a smaller absorption coefficient than the reduced scattering coefficient by directing an optical beam obliquely incident to the medium and determining the reduced scattering coefficient as a function of the distance between the incident point and the center of the diffused reflectance, the incident angle, the relative refractive index and the reduced scattering coefficient.

8 Claims, 10 Drawing Sheets

METHOD OF MEASURING TISSUE OPTICAL PROPERTIES USING AN OPTICAL BEAM OF OBLIQUE INCIDENCE AND USES THEREOF

BACKGROUND OF THE INVENTION

1. Field of the Invention

The present invention relates generally to the fields of optics, lasers and medical diagnostics. More specifically, the present invention relates to a novel method of measuring tissue optical properties using a optical beam of oblique incidence and uses thereof.

2. Description of the Related Art

In both diagnostic and therapeutic applications of light in medicine, it is important to evaluate optical properties of tissues, including the absorption coefficient ($\mu_a$) and the reduced scattering coefficient [$\mu_s'=\mu_s(1-g)$], where $\mu_s$ is the scattering coefficient and g is the anisotropy factor of scattering. The optical properties can be used to diagnose diseases, to measure tissue metabolic status, or to determine the dosimetry in therapeutic applications of lasers. Measuring optical properties of tissues in vitro can be accomplished by several techniques, with the integrating sphere measurement as the most common (Pickering, J. W. et al., Appl. Opt.; 32:399–410 (1993)). Measuring optical properties of tissues in vivo is still a challenge.

Wilson et al. (Wilson, B. C. et al., Proc. Soc. Photo-Opt. Instrum. Eng.; IS6:219–232 (1990)) have used an optical fiber bundle and Jacques et al. (Jacques S. L. et al., Proc. Soc. Photo-Opt. Instrum. Eng.; IS11:211–226 (1993)) a video reflectometer to measure diffuse reflectance of tissues in vivo. Diffusion theory has been used to compute diffuse reflectance to deduce optical properties. Diffusion theory is valid for an infinitely narrow laser beam and for observation points far from the light source, but a laser beam of a finite size is used for measurement of diffuse reflectance. Therefore, diffusion theory is only approximately correct. Another method represented by Patterson et al. uses the falling tail of time-resolved diffuse reflectance to deduce tissue optical properties but requires expensive instrumentation.

The prior art is deficient in the lack of an accurate method of measuring tissue optical properties. The present invention fulfills this longstanding need and desire in the art.

SUMMARY OF THE INVENTION

A new simple and quick approach was used to measure the reduced scattering coefficient ($\mu_s'$) of a semi-infinite turbid medium having a much smaller absorption coefficient than reduced scattering coefficient. A laser beam with an oblique angle of incidence to the medium caused the center of the diffuse reflectance that is several transport mean free paths away from the incident point to shift away from the point of incidence by an amount $\Delta x$. This amount was used to compute the reduced scattering coefficient by $\mu_s'=\sin(\alpha_i)/(n \, \Delta x)$, where n is the refractive index of the turbid medium divided by that of the incident medium, and $\alpha_i$ is the angle of incidence measured from the surface normal. For a turbid medium having a comparable absorption coefficient with $\mu_s'$, a revision to the above formula was made. This method was tested theoretically by Monte Carlo simulations and experimentally by a video reflectometer.

In one embodiment of the present invention, there is provided a method of determining the reduced scattering coefficient of a medium having a smaller absorption coefficient than the reduced scattering coefficient of a medium, comprising the steps of: directly an optical beam that is obliquely incident upon said medium; determining the reduced scattering coefficient of the medium using the diffuse reflectance profile based on the following formula:

$$\Delta x = \frac{\sin(\alpha_i)}{n \cdot \mu_s'}$$

wherein $\Delta x$ is the distance between the incident point and the center of the diffuse reflectance that is several transport mean free paths away from the center; $\alpha_i$ is the incident angle; n is the relative refractive index; and $\mu_s'$ is the reduced scattering coefficient.

In another embodiment of the present invention, there is provided a method of determining the reduced scattering coefficient of a medium having an absorption coefficient similar to the reduced scattering coefficient of the medium, comprising the steps of: directly an optical beam that is obliquely incident upon said medium; determining the reduced scattering coefficient of the medium using the diffuse reflectance profile based on the following formula:

$$\Delta x = \frac{\sin(\alpha_i)}{n(\mu_s' + 0.35 \mu_a)}$$

wherein $\Delta x$ is the distance between the incident point and the center of the diffuse reflectance that is several transport mean free paths away from the center;

$\alpha_i$ is the incident angle;

n is the relative refractive index;

$\mu_a$ is the absorption coefficient; and $\mu_s'$ is the reduced scattering coefficient.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 5 shows that CCD video images of a diffuse reflectance pattern from a turbid medium with the same optical properties as those in FIG. 3. The resolution of the images was 8.5×10$^{-3}$ cm/pixel.

DETAILED DESCRIPTION OF THE INVENTION

Definitions

Figure 1A:
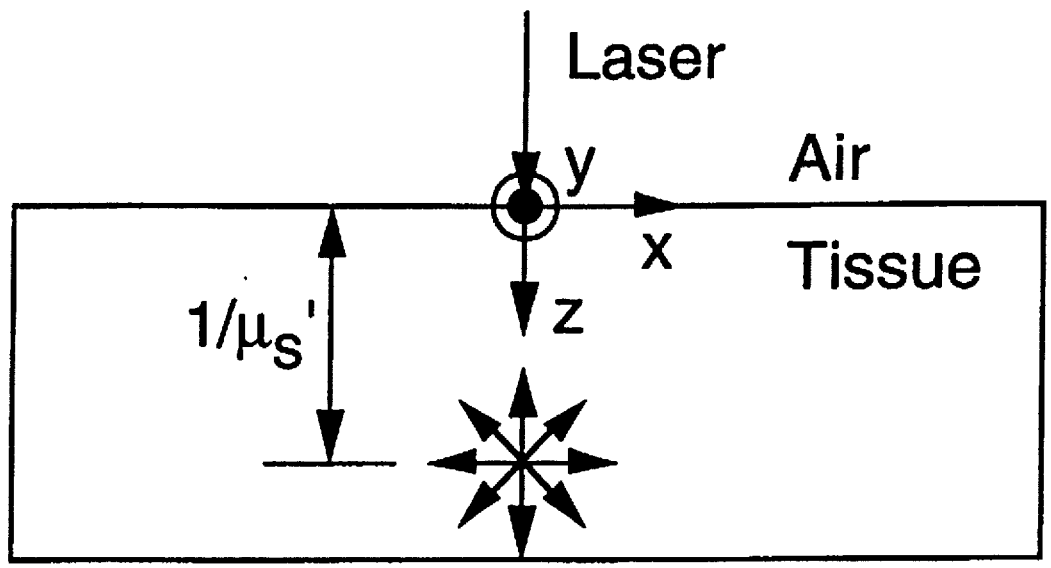
FIG. 1A shows a lumped isotropic point source for a laser beam of (a) normal incidence ($\alpha_i=0$) and (b) oblique incidence ($\alpha_i>0°$). A coordinate system was set up in which the y-axis pointed outward from the paper.

As used herein, the term "tissue optics" refers to light propagation in biological tissues and "optical properties" refers to absorption and scattering properties of tissues.

As used herein, the term "turbid media" refers to media that scatters light and often times absorbs light as well. Most biological tissues are turbid media.

As used herein, the term "scattering media" refers to media that acatters light and often times absorbs light as well.

As used herein, the term "absorption coefficient" refers to the probability of light absorption per unit path-length.

As used herein, the term "reduced scattering coefficient" refers to the probability of equivalently isotropic scattering per unit path-length.

As used herein, the term "Monte Carlo simulation" refers to a statistical method that can be used to trace photon propagation in turbid media.

As used herein, the term "interaction coefficient" refers to the probability of light absorption or scattering per unit path-length.

As used herein, the term "Mean free path [mfp]" refers to the mean path-length between photon-medium interactions which can be either absorption or scattering.

As used herein, the term "penetration depth" refers to how quickly light intensity decays in turbid media. Penetration depth is determined by both absorption and scattering properties of turbid media.

In the present invention, a method is used that deduces reduced scattering coefficient very quickly and is independent of the laser beam size if the laser beam has a predefined mirror symmetry and the size of the beam is smaller than the distance between the observation points and the center of the laser beam. For example, a circular flat beam or a circular Gaussian beam has an elliptic spot on the medium surface when the beam is incident at an oblique angle. The mirror symmetry of this elliptic spot about its short axis allows the application of this method to measure the reduced scattering coefficient.

The present invention is directed to a novel method of determining the reduced scattering coefficient of a turbid medium having an absorption coefficient less than the reduced scattering coefficient of said medium, comprising the steps of: directing an optical beam that is obliquely incident upon said medium; determining the reduced scattering coefficient of the medium using the diffuse reflectance profile based on the following formula:

$$\Delta x = \frac{\sin(\alpha_i)}{n \cdot \mu_s'}$$

wherein $\Delta x$ is the distance between the incident point and the center of the diffuse reflectance that is several transport mean free paths away from the center; $\alpha_i$ is the incident angle; n is the relative refractive index; and $\mu_s'$ is the reduced scattering coefficient.

Although the novel method of the present invention may be practiced on any turbid medium, preferably the turbid medium is a biological sample.

Generally, the optical beam used in the methods of the present invention is directed at the medium at an oblique angle. Preferably, the angle of said optical beam is from about 5° to about 85°. Preferably, the absorption coefficient less than about 10% of the reduced scattering coefficient of said medium.

The present invention is also directed to a method of determining an optical property of a turbid medium having an absorption coefficient similar to the reduced scattering coefficient of the medium, comprising the steps of: directing an optical beam that is obliquely incident upon said medium; determining the reduced scattering coefficient of the medium using the diffuse reflectance profile based on the following formula:

$$\Delta x = \frac{\text{Sin}(\alpha_i)}{n(\mu_s' + 0.35 \mu_a)}$$

wherein $\Delta x$ is the distance between the incident point and the center of the diffuse reflectance that is several transport mean free paths away from the center; $\alpha_i$ is the incident angle; n is the relative refractive index; $\mu a$ is the absorption coefficient; and $\mu_s'$ is the reduced scattering coefficient.

The following examples are given for the purpose of illustrating various embodiments of the invention and are not meant to limit the present invention in any fashion.

EXAMPLE 1

For a semi-infinite tissue whose $\mu_a<<\mu_s'$, a narrow laser beam with normal incidence can be approximately represented by a buried isotropic point source [FIG. 1(a)]. The laser beam's diffuse reflectance that is several transport mean free paths away from the incident point is well approximated by that of such an isotropic point source. The point source is one scattering mean free path $1/\mu_s'$ below the tissue surface, which is approximately equal to one transport mean free path $1/(\mu_a+\mu_s')$ because $\mu_a<<\mu_s'$. For a semi-infinite turbid medium with optical properties $\mu_a=0.1$ cm$^{-1}$, $\mu_s=100$ cm$^{-1}$, g=0.9, the relative error in diffuse reflectance between the diffusion theory and the Monte Carlo simulation is <15% at x=0.1 cm and <10% for x>0.2 cm (Wang L. H. et al., Proc. Soc. Photo-Opt. Instrum. Eng.; 1888:107–166 (1993)). The Monte Carlo simulated results were considered accurate and were used as the standard to evaluate the accuracy of the diffusion theory.

Figure 1B:
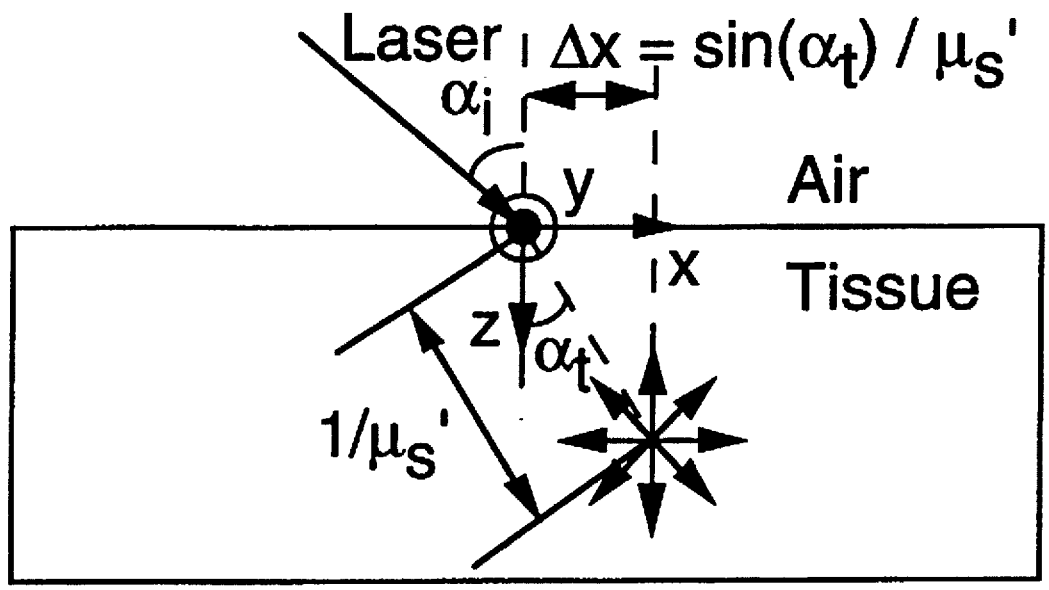

Similarly, a laser beam with oblique incidence can be approximated by an isotropic point source that is $1/\mu_s'$ away from the laser point of incidence along the unscattered-light transmission path, which is usually refracted away from the original incident direction [FIG. 1B]. As a result, the isotropic point source is horizontally shifted away from the point of incidence by $$\Delta x = \sin(\alpha_t)/\mu_s' = \sin(\alpha_i)/(n\, \mu_s'), \quad (1)$$

where $\alpha_i$ and $\alpha_t$ are the angles of incidence and transmission, respectively, and n is the refractive index of the tissue divided by that of the ambient medium. If the oblique laser beam's diffuse reflectance that is several transport mean free paths away from the incident point can be approximated by that of the isotropic point source, the center of this diffuse reflectance will be shifted from the point of incidence by the same amount $\Delta x$. The following sections describe the testing and revision of Eq. (1) for a better accuracy when $\mu_a<<\mu_s'$ does not hold.

EXAMPLE 2

To test Eq. (1) theoretically, Monte Carlo modeling (1) was used to simulate the diffuse reflectance for a laser beam with various angles of incidence to a semi-infinite turbid medium of various optical properties. The number of photon packets used for the simulations ranged between 500,000 and 5,000,000, depending on the incident angle and optical properties such that the computational time for each simulation on a Sun SPARCstation 10 computer did not exceed 24 hours. The center line of the diffuse reflectance as a function of x was obtained from the reflectance curve, where the center line consisted of midpoints between the left and right sides of the diffuse reflectance for each reflectance value. The spatial difference between the vertical portion of the center line and the incident point yielded the shift $\Delta x$. The shift values as a function of the incident angles and optical properties were used to compare with Eq. (1).

Figure 2:
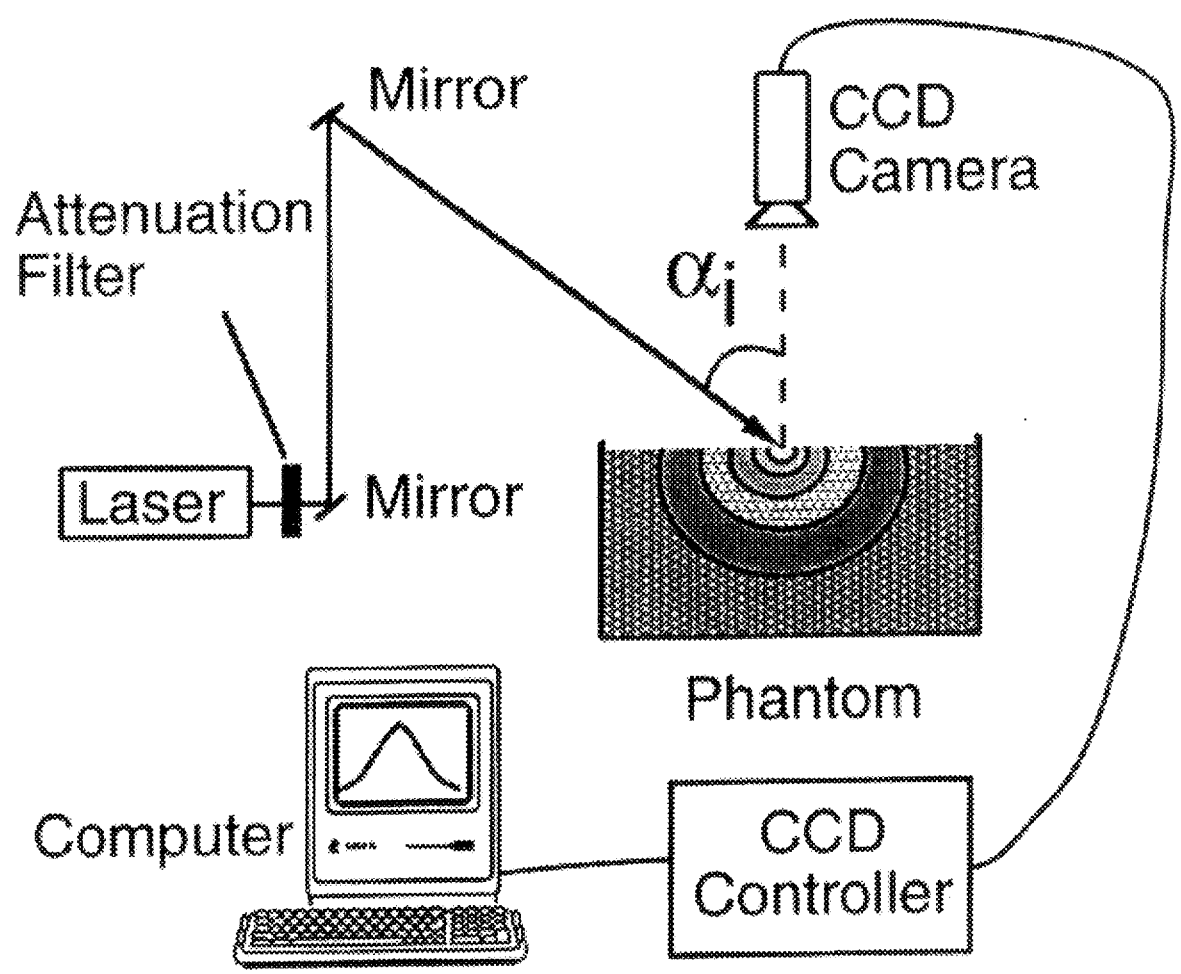
FIG. 2 shows a schematic of the video reflectometer.

To test Equation (1) experimentally, a video reflectometer was used to measure the diffuse reflectance from a tissue-simulating turbid medium (FIG. 2). Light from a He—Ne laser (output, 5 mW; wavelength, 632.8 nm) was directed to the medium surface at $\alpha_i=49°$. The eight-bit video CCD (charge-coupled device) camera measured the diffuse reflectance, and the computer collected and then analyzed the CCD image. The dynamic range of the CCD is limited to 255 and is further reduced by the consideration of a good signal to noise ratio. Therefore, two images with different intensities of the laser beam were taken to measure the diffuse reflectance in a wider surface area. Then, the diffuse reflectance was analyzed to test Eq. (1).

A proof in the Appendix shows that the shift $\Delta x$ is independent of the size of the laser beam if the laser spot on the medium surface has a mirror symmetry about the y-axis in FIG. 1. Of course, the size of the beam should be smaller than the distance between the observation points and the center of the laser beam because the analysis in the hypothesis is valid only for the observation points that are several transport mean free paths away from the light source. The laser beam had an elliptic shape on the surface of the turbid medium and hence had a mirror symmetry about the y-axis. Therefore, this independence validates the above experiment with a laser beam of a finite size instead of an ideal laser beam of an infinitely small size.

EXAMPLE 3

The tissue-simulating turbid medium consisted of de-ionized water mixed with minimally scattering trypan blue dye as the absorbers and minimally absorbing polystyrene spheres (diameter, 579±21 nm) as the scatterers. The $\mu_a$ of the original dye and the $\mu_s$ of the original sphere solution were measured using collimated transmission, and the g of the spheres was computed using Mie theory based on the diameter of the spheres and the refractive indices of the spheres (1.56) and of the water (1.33). Then, the optical properties of the mixed turbid medium were computed according to the volume concentrations of the two original components in the mixture. The optical properties of the turbid medium for this experiment were n=1.33, $\mu_a=0.25$ cm$^{-1}$, $\mu_s=20$ cm$^{-1}$, and g=0.853. The reduced scattering coefficient was computed to be $\mu_s'=2.94$ cm$^{-1}$.

EXAMPLE 4

Figure 3:
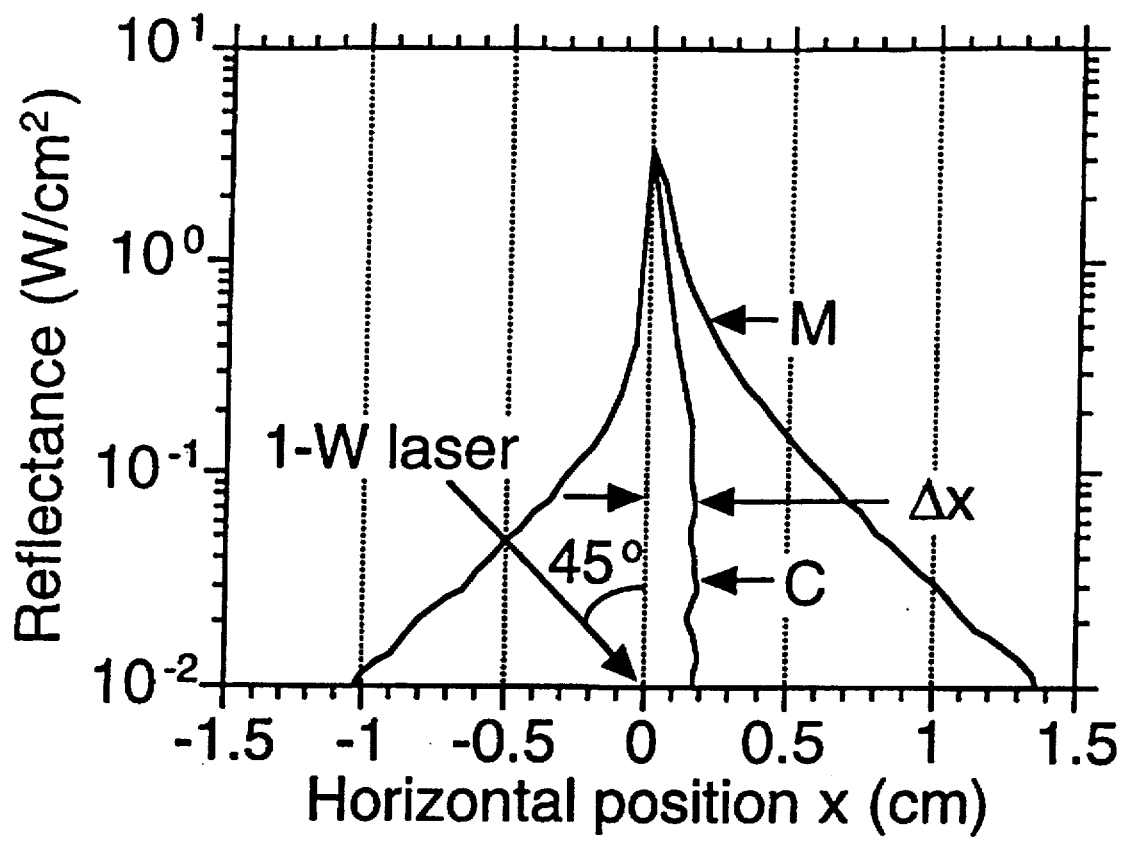
FIG. 3 shows that curve M is the Monte Carlo simulated diffuse reflectance of a 1-W laser beam incident to a turbid medium with $\alpha_i=45°$, and curve C is the center line of curve M, i.e., the midpoint of the left and right sides of curve M for specific reflectance values. The optical properties of the turbid medium were n=1.33, $\mu_a=0.25$ cm$^{-1}$, $\mu_s=20$ cm$^{-1}$, and g=0.853.

FIG. 3 shows the diffuse reflectance computed using the Monte Carlo model. The optical properties of the turbid medium used in the simulation were chosen to be those of the tissue-simulating turbid medium used in the experiment. The shift based on the vertical portion of curve C was $\Delta x=0.174\pm0.009$ cm, and the shift based on Eq. (1) and the optical properties was $\Delta x=0.181$ cm. The standard error of the shift computed with the Monte Carlo model was caused by the statistical nature of Monte Carlo simulations. The two values of the shift were in agreement but the accuracy of Eq. (1) can be improved based on more Monte Carlo simulations as shown below.

Figure 4A:
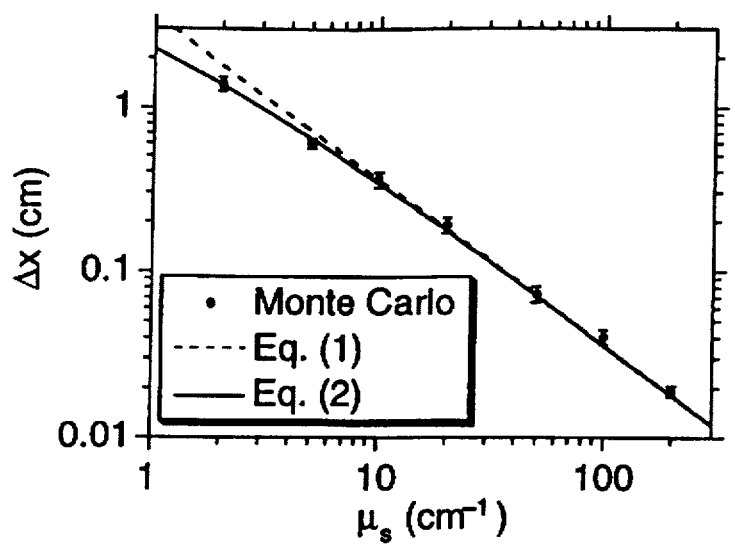
FIG. 4 shows that the symbols with error bars were Monte Carlo-simulated $\Delta x$ for different (a) $\mu_s$, (b) $\mu_a$, and (c) angles of incidence $\alpha_i$. The dashed and solid lines were computed using Eqs. (1) and (2), respectively. The parameters for FIG. 4(a) were $\alpha_i=45°$, n=1.33, $\mu_a=0.25$ cm$^{-1}$, various $\mu_s$, and g=0.853. The parameters for FIG. 4(b) were $\alpha_i=45°$, n=1.33, various $\mu_a$, $\mu_s=20$ cm$^{-1}$, and g=0.853. The parameters for FIG. 4(c) were various $\alpha_i$, n=1.33, $\mu_a=0.25$ cm$^{-1}$, $\mu_s=20$ cm$^{-1}$, and g=0.853.

FIG. 4A shows the shift values computed using the Monte Carlo simulations for various $\mu_s$ values of the turbid media. The dashed line is based on Eq. (1) and deviates from the Monte Carlo simulated data for small $\mu_s'$ values. The deviation was considered to be caused by the increased effect of $\mu_a$ for decreased $\mu_s'$ and can be reduced by adding the weighted $\mu_a$ to $\mu_s'$. Based on this consideration, the computed shift values were found to be fit the best by $$\Delta x = \sin(\alpha_i)/[n(\mu_s' + 0.35\ \mu_a)], \quad (2)$$

where $\alpha_i=45°$, n=1.33, $\mu_a=0.25$ cm$^{-1}$, $\mu''=\mu_s(1-0.853)$, and the term 0.35 $\mu_a$ was introduced to minimize the fitting error. Least-squares fit was used to determine the coefficient in front of the $\mu_a$ in Eq. (2), and the fitting correlation coefficient between the raw data and Eq. (2) was 0.999.

Figure 4B:
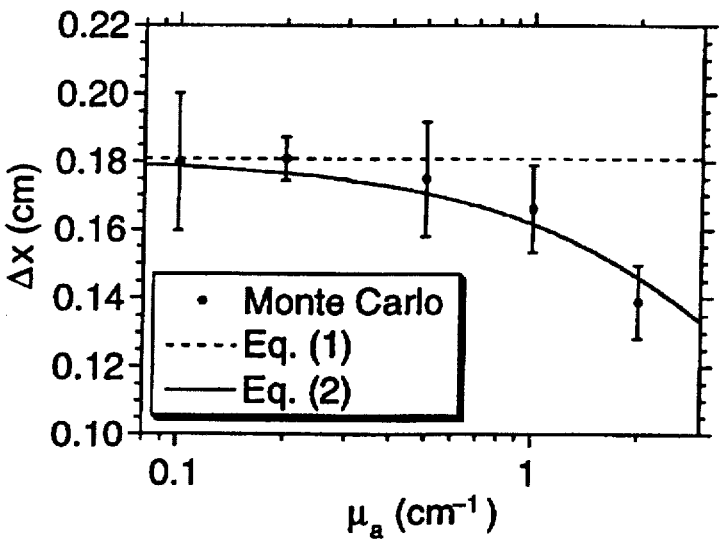

FIG. 4B shows the shift values computed using the Monte Carlo simulations for various $\mu_a$ values of the turbid media, where $\alpha_i=45°$, n=1.33, $\mu_s'=20$ cm$^{-1}\times(1-0.853)=2.94$ cm$^{-1}$. Eq. (1) fit the data points with low $\mu_a$ values and deviated from those with high $\mu_a$ values, while Eq. (2) fit the raw data very well.

Figure 4C:
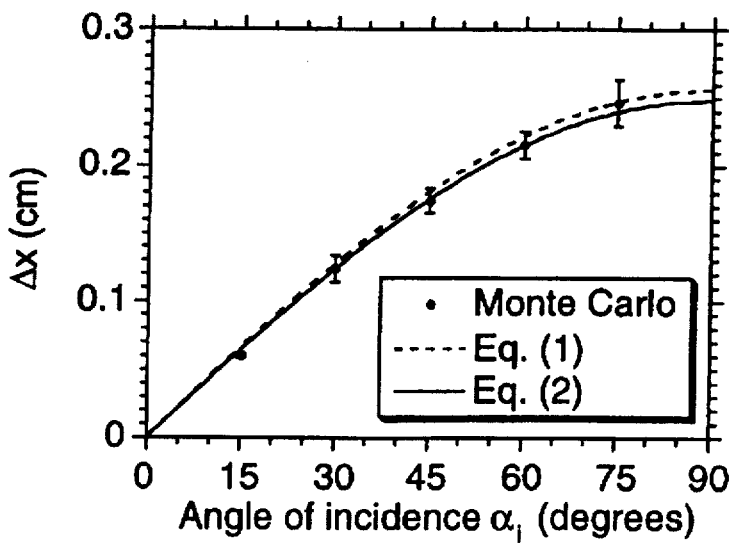

FIG. 4C shows the shift values computed using the Monte Carlo simulations for various incident angles $\alpha_i$. Both Eqs. (1) and (2) fit the raw data well because $\mu_a<<\mu_s'$ in this case, where n=1.33, $\mu_a=0.25$ cm$^{-1}$, $\mu_s'=20$ cm$^{-1}\times(1-0.853)=2.94$ cm$^{-1}$.

Figure 5A:
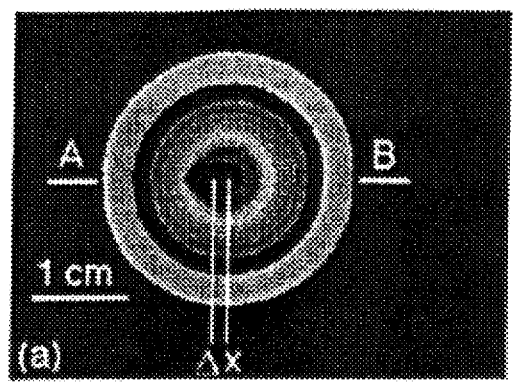
FIG. 5A shows a video image without laser beam attenuation. The center of the image was saturated on the CCD camera.
Figure 5B:
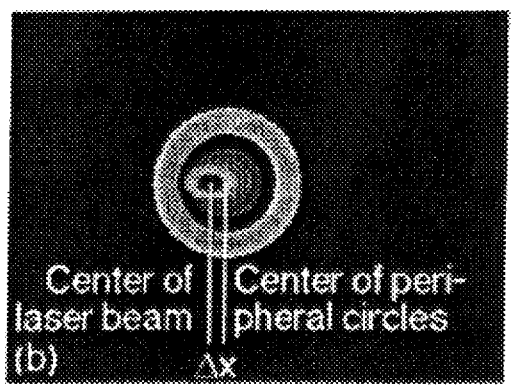
FIG. 5B shows a video image with a 3.3-fold attenuation by a filter to measure the saturated center portion of FIG. 5A.
Figure 5C:
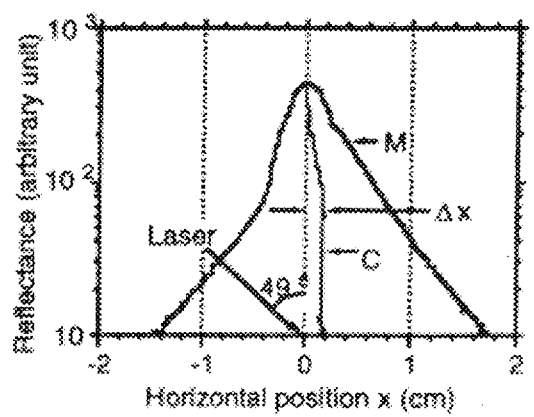
FIG. 5C shows the diffuse reflectance along the x-axis.
Figure 6:
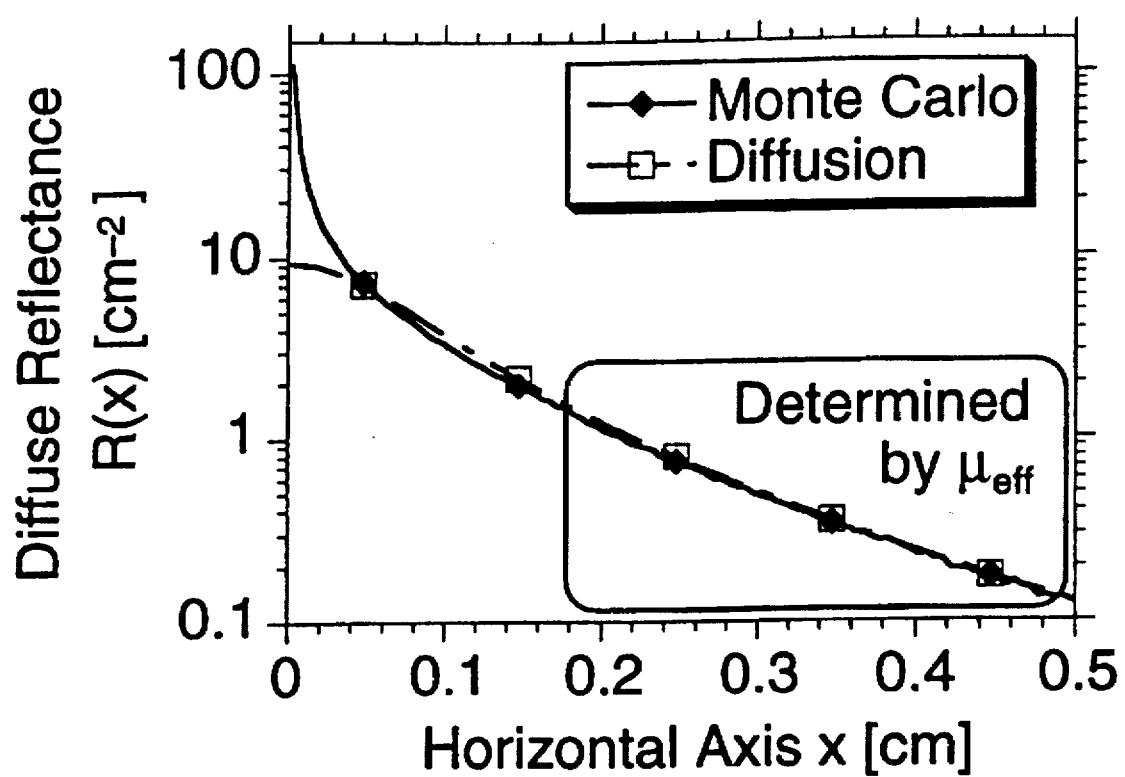
FIG. 6 shows the diffuse reflectance of a laser beam normally incident upon a semi-infinite turbid medium as a function of x, which is the distance between the observation point and the incident point of the laser beam (see FIG. 7). The computation was based on Monte Carlo simulation and diffusion theory. The optical properties of the turbid medium are index of refraction n=1.0, absorption coefficient $\mu_a=0.1$ cm$^{-1}$, scattering coefficient $\mu_s=100$ cm$^{-1}$, anisotropy g=0.9.
Figure 7:
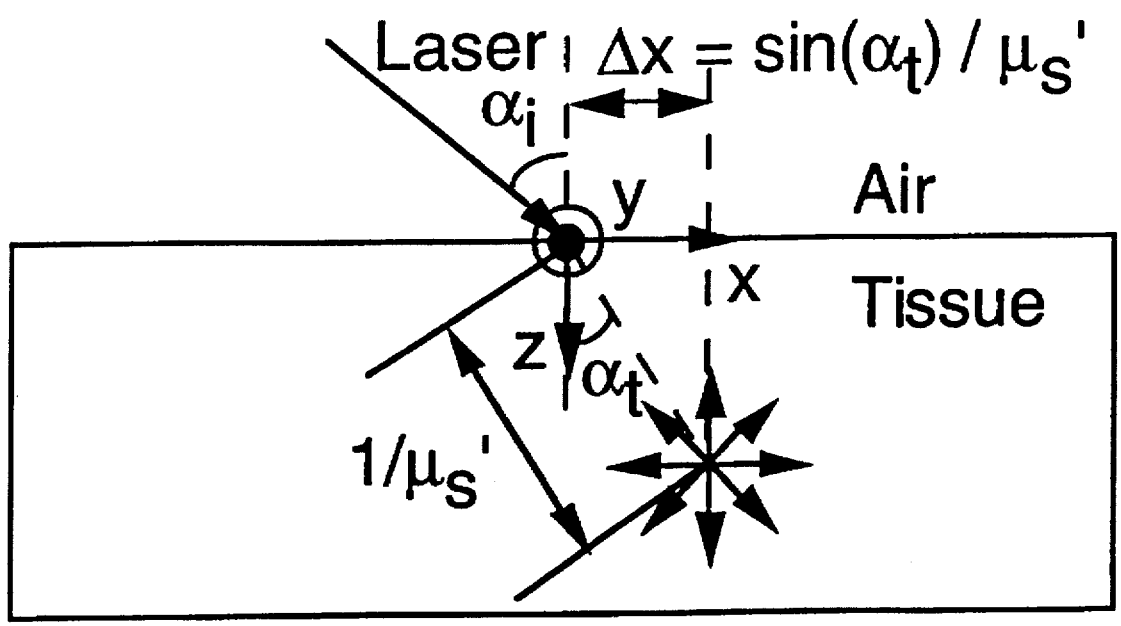
FIG. 7 shows a coordinate system and the lumped interaction approximation of the laser beam. In the FIG., $\alpha_i$ is the incident angle of the laser beam, $\alpha_t$ is the refracted angle, $\Delta x$ is the horizontal shift of the lumped interaction site from the incident point. The y-axis point outward from the paper.
Figure 8:
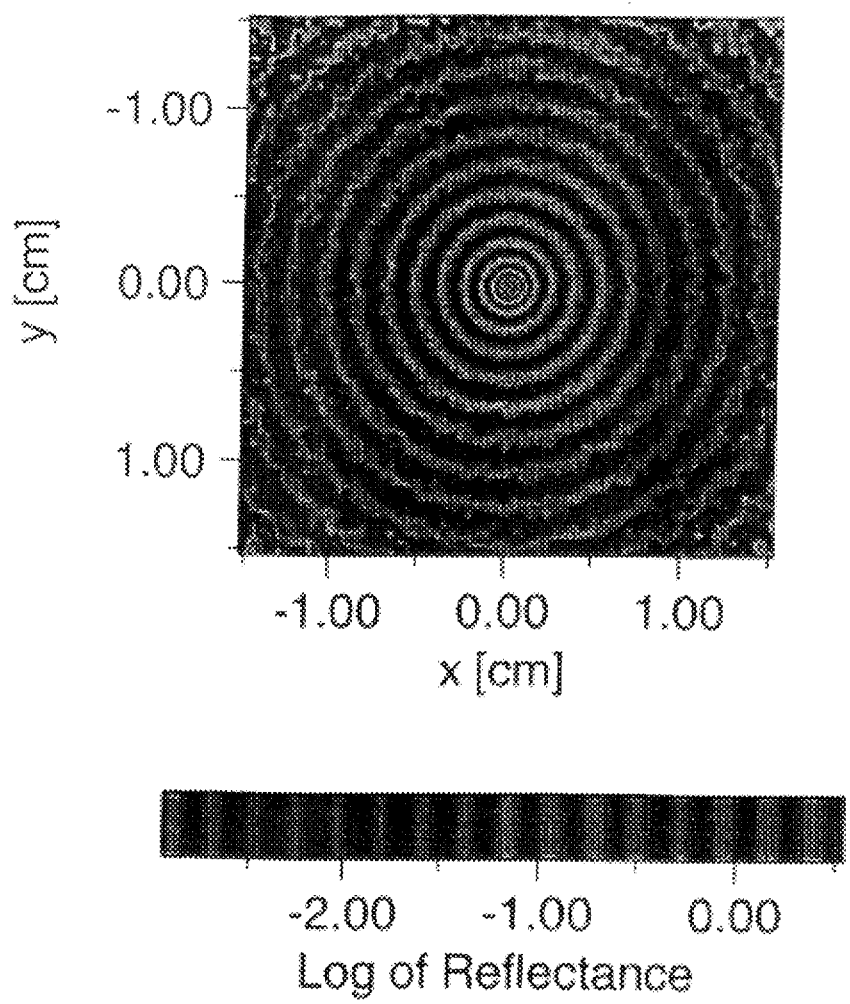
FIG. 8 shows a two dimensional distribution of diffuse reflectance of a normally incident laser beam ($\alpha_i=0$) computed with Monte Carlo simulations. Each ring represents a contour line of diffuse reflectance. The bottom bar is the palette used to generate the plot. The optical properties of the semi-infinite turbid medium are index of refraction n=1.33, absorption coefficient $\mu_a=0.25$ cm$^{-1}$, scattering coefficient $\mu_s=20$ cm$^{-1}$, anisotropy g=0.853.
Figure 9:
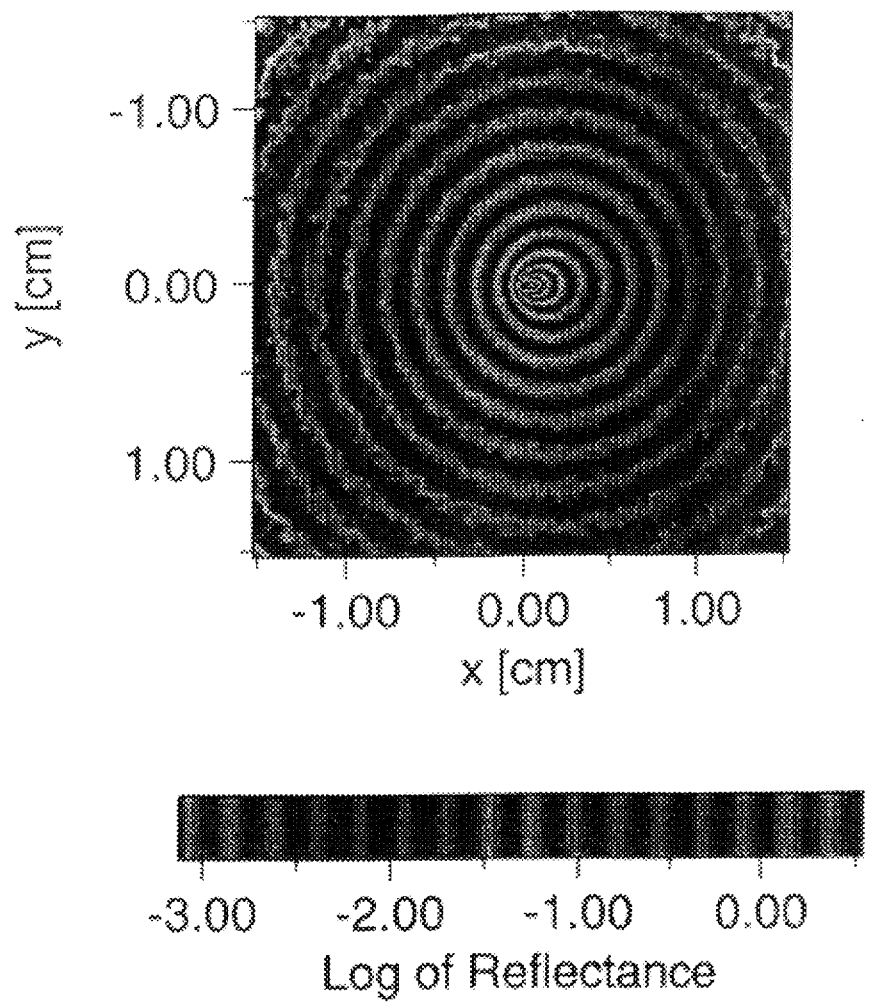
FIG. 9 shows a two dimensional distribution of diffuse reflectance of an obliquely incident laser beam ($\alpha_i=45°$) computed with Monte Carlo simulations. Each ring represents a contour line of diffuse reflectance. The bottom bar is the palette was used to generate the plot. The optical properties of the semi-infinite turbid medium are index of refraction n=1.33, absorption coefficient $\mu_a=0.25$ cm$^{-1}$, scattering coefficient $\mu_s=20$ cm$^{-1}$, anisotropy g=0.853.
Figure 10:
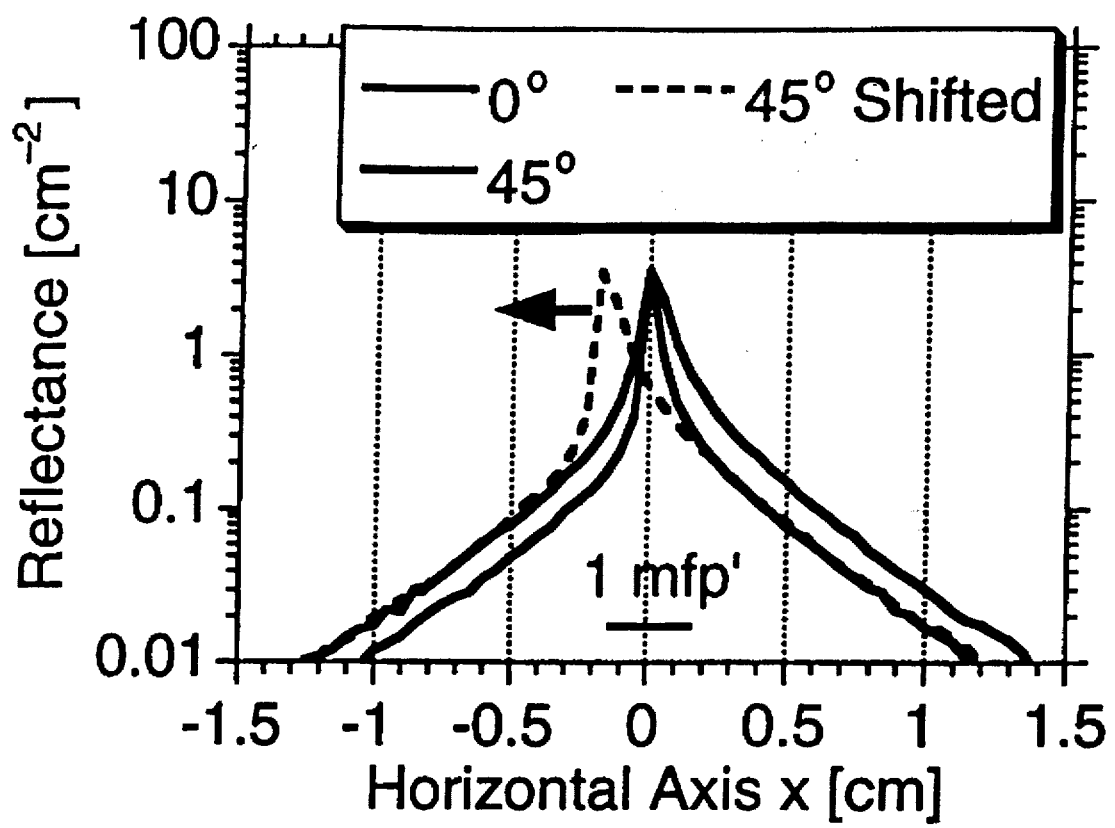
FIG. 10 shows the diffuse reflectance distributions along the x-axis in FIGS. 8 and 9. The slopes of the two curves become parallel far away from the incident point of the laser beam. Once the diffuse reflectance curve of the 45 degree incidence was translated, its slope matches that of the diffuse reflectance curve of the normal incidence.

FIG. 5 shows the experimental results using a video reflectometer described in FIG. 2. Because the laser beam was oblique to the surface, the reflectance pattern was asymmetrical near the point of incidence, but the diffuse reflectance far from the source formed concentric circles [FIG. 5A and FIG. 5B]. Selecting the reflectance values along the x-axis of each image, e.g., along the horizontal line crossing from A to B in FIG. 5A, and replacing the saturated center portion of FIG. 5A with the corresponding portion in FIG. 5B compensated by the attenuation factor, the diffuse reflectance as a function of x was plotted in FIG. 5C. The peak reflectance occurred at the center of the incident laser beam and defined the origin of the x-axis in FIG. 5C. The circular periphery that is several transport mean free paths away from the incident point defined an apparent center [FIG. 5A and 5B] that was offset from the origin by $\Delta x$ and yielded a vertical center line [FIG. 5C that shared the same physical meaning with the apparent center. The experimental shift $\Delta x$ in FIG. 5C was $0.172\pm0.003$ cm. Based on Eq. (2), the theoretical shift value was computed to be 0.187 cm, where $\alpha_i=49°$, n=1.33, $\mu_a=0.25$ cm$^{-1}$, $\mu_s'=2.94$ cm$^{-1}$. The relative error between the experimental and theoretical shift values was 8%.

EXAMPLE 5

Eq. (2) is a refined version of Eq. (1) and reduces to Eq. (1) when $\mu_a<<\mu_s'$. Eq. (1) is valid only when $\mu_a<<\mu_s'$, whereas Eq. (2) is valid even when $\mu_a$ is comparable with $\mu_s'$. The computed shift value in FIG. 3 was 0.176 cm when based on Eq. (2) instead of 0.181 cm when based on Eq. (1), and 0.176 cm was in better agreement with the shift value $0.174\pm0.009$ cm computed using the Monte Carlo simulations.

Eq. (2) fit the Monte Carlo simulation results in FIG. 4 very well for different optical properties and incident angles and agreed with the video reflectometry measurement with an 8% error. The experiment used an eight-bit CCD camera, and two measurements with and without the attenuation of the laser source intensity were needed. The neutral density filter may shift the center of the laser beam slightly. The difference between the theoretical and experimental shift values was 0.015 cm, only 1.8 pixels on the CCD camera because the resolution in the set up was $8.5\times10^{-3}$ cm/pixel. Therefore, the accuracy of the experiment was limited by the resolution and the dynamic range of the camera.

When $\mu_a<<\mu_s'$, e.g., $\mu_a=0.1$ cm$^{-1}$ and $\mu_s'=10$ cm$^{-1}$ (which are typical for biological tissues at visible wavelengths), Eq. (2) is reduced to the simpler Eq. (1). Since $\alpha_i$ and n are known, Eq. (1) demonstrates that if one measures the diffuse reflectance of a laser beam with oblique incidence and compute $\Delta x$, then one can calculate $\mu_s'$ using $$\mu_s' = \sin(\alpha_i)/(n\ \Delta x). \quad (3)$$

This equation useful in the methods of the present invention provides a very simple approach for measuring the reduced scattering coefficient that can be applied to biological tissues for diagnosis of disease in clinical settings.

When $\mu_a$ is comparable with $\mu_s'$, then $\mu_s'$ cannot be solved from the measurement of $\Delta x$ independently. Another technique may be used in combination with this method to determine both $\mu_a$ and $\mu_s'$. For example, the falling tail of time-resolved diffuse reflectance can be used to determine $\mu_a$ (Patterson, M. S. et al.; Appl. Opt.; 28:2331–2336 (1989)).

In summary, the validity of this new methodology of the present invention used to measure reduced scattering coefficients of turbid media was theoretically and experimentally demonstrated. The approach is straightforward and quick, thus has great utility in a wide variety of clinical applications.

EXAMPLE 6

This appendix provides a mathematical proof showing that the shift value is independent of the size of the incident laser beam if the beam has a mirror symmetry about the y-axis (FIG. 1) and the size of the laser beam is smaller than the distance between the observation points and the incident point. Assuming that an infinitely narrow laser beam's diffuse reflectance that is several transport mean free paths away from the incident point, G(x, y), has a mirror symmetry about $x=\Delta x$ (FIG. 1), i.e., $G(\Delta x-x, y)=G(\Delta x+x, y)$, if a laser beam of a finite size with an intensity profile S(x, y) has a mirror symmetry about the y-axis, i.e., $S(-x, y)=S(x, y)$, then this finite-size laser beam's diffuse reflectance that is several transport mean free paths away from the incident point, R(x, y), will also have a mirror symmetry about $x=\Delta x$.

Since the turbid medium is semi-infinite, R(x, y) can be expressed with a convolution $$R(x,y) = \int_{-\infty}^{+\infty}\int_{-\infty}^{+\infty} S(x',y')G(x-x',y-y')dx'dy', \quad (A-1)$$

and one obtains $$\begin{aligned}R(\Delta x-x,y) &= \int_{-\infty}^{+\infty}\int_{-\infty}^{+\infty} S(x',y') \times \\ & \quad G(\Delta x-x-x',y-y')dx'dy', \\ &= \int_{-\infty}^{+\infty}\int_{-\infty}^{+\infty} S(x',y') \times \\ & \quad G(\Delta x+x+x',y-y')dx'dy', \\ &= \int_{+\infty}^{-\infty}\int_{-\infty}^{+\infty} S(-x',y') \times \\ & \quad G(\Delta x+x-x',y-y')d(-x')dy', \\ &= \int_{-\infty}^{+\infty}\int_{-\infty}^{+\infty} S(x',y') \times \\ & \quad G(\Delta x+x-x',y-y')dx'dy', \\ &= R(\Delta x+x,y),\end{aligned} \quad (A2)$$

which means that R(x, y) has a mirror symmetry about $x=\Delta x$.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of determining the reduced scattering coefficient of a turbid medium having an absorption coefficient less than the reduced scattering coefficient of said medium, comprising the steps of:

directing an optical beam that is obliquely incident upon said medium;

determining the reduced scattering coefficient of the medium using the diffuse reflectance profile based on the following formula:

$$\Delta x = \frac{\sin(\alpha_i)}{n \cdot \mu_s'}$$

wherein $\Delta x$ is the distance between the incident point and the center of the diffuse reflectance that is several transport mean free paths away from the center;

$\alpha_i$ is the incident angle;

n is the relative refractive index; and $\mu_s'$ is the reduced scattering coefficient.

2. The method of claim 1, wherein said turbid medium is a biological sample.

3. The method of claim 1, wherein the angle of said optical beam is from about 5° to about 85°.

4. The method of claim 1, wherein the absorption coefficient less than about 10% of the reduced scattering coefficient of said medium.

5. A method of determining an optical property of a turbid medium having an absorption coefficient similar to the reduced scattering coefficient of the medium, comprising the steps of:

directing an optical beam that is obliquely incident upon said medium;

determining the reduced scattering coefficient of the medium using the diffuse reflectance profile based on the following formula:

$$\Delta x = \frac{\sin(\alpha_i)}{n(\mu_s' + 0.35\mu_a)}$$

wherein $\Delta x$ is the distance between the incident point and the center of the diffuse reflectance that is several transport mean free paths away from the center;

$\alpha_i$ is the incident angle;

n is the relative refractive index;

$\mu_a$ is the absorption coefficient; and $\mu_s'$ is the reduced scattering coefficient.

6. The method of claim 5, wherein said turbid medium is a biological sample.

7. The method of claim 5, wherein the angle of said optical beam is from about 5° to about 85°.

8. The method of claim 5, wherein said optical property is selected from the group consisting of absorption coefficient.

* * * * *

UNITED STATES PATENT AND TRADEMARK OFFICE
CERTIFICATE OF CORRECTION

PATENT NO. : 5,630,423
DATED : May 20, 1997
INVENTOR(S) : Wang, et al.

It is certified that error appears in the above-identified patent and that said Letters Patent is hereby corrected as shown below:

Column 3, line 63, after "that", delete "acatters" and insert -- scatters --.

Column 5, line 29, after "107", delete "166" and insert -- 116 --.

Column 6, line 6, after "a", delete "He--Ne", and insert -- He-Ne --.

Column 7, line 5, after "cm$^{-1}$", delete "$\mu^s$, and insert -- $\mu_s'$ --.

Signed and Sealed this

Eleventh Day of November, 1997

Attest:

BRUCE LEHMAN

Attesting Officer

Commissioner of Patents and Trademarks